United States Patent [19]

Saville

[11] Patent Number: Plant 6,570

[45] Date of Patent: Jan. 31, 1989

[54] ROSE PLANT NAMED SAVAREND

[75] Inventor: F. Harmon Saville, Rowley, Mass.

[73] Assignee: Nor'East Miniature Roses, Inc., Rowley, Mass.

[21] Appl. No.: 62,068

[22] Filed: Jun. 15, 1987

[51] Int. Cl.[4] ..... A01H 5/00

[52] U.S. Cl. ..... Plt./9

[58] Field of Search ..... Plt./9

*Primary Examiner*—Robert E. Bagwill
*Attorney, Agent, or Firm*—Vincent G. Gioia

[57] ABSTRACT

A new unusual exhibition style red miniature rose variety.

1 Drawing Sheet

1

The present invention relates to a new and distinct variety of rose plant of the miniature rose class, which was originated by my crossing as seed parent an unnamed, unpatented seedling of my creation and as pollen parent the rose known as "Rainbow's End". The denomination of this new rose is "Savarend".

Among the novel characteristics possessed by this new variety which distinguish it from its parents and all other varieties of which I am aware are its unusual red flowers of excellent exhibition hybrid tea-like form and which are long lasting on the plant and after cutting. Asexual reproduction by budding of the new variety as performed in San Bernardino County, Calif. shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Colour Chart (RHSCC). The terminology used in color description herein refers to plate numbers in the aforementioned color chart, e.g., "54A" is plate 54A of the Royal Horticultural Society Colour Chart.

Parentage: Seedling.
*Seed parent.*—Unnamed seedling.
*Pollen parent.*—"Rainbow's End".
Class: Miniature.

The following observations are made of specimens grown outdoors in San Bernardino County, Calif., during the month of April.

FLOWER

Blooming habit: Recurrent.

A. Bud:
(1) *Size.*—Medium.
(2) *Form.*—Long pointed.
(3) *Color.*—As sepals separate, bud color is near Spinel Red 54A.
(4) *Sepals.*—Relatively unfoliated, longer than bud.
(5) *Peduncle.*—Length — about 1¼ inch. Aspect — straight. Strength — erect. Color — near 177A.

B. Bloom:

2

(1) *Size.*—Average size when fully expanded — about 1¾ inches.
(2) *Borne.*—Singly, one to a stem and several together in sprays.
(3) *Form.*—Exhibition style, high centered until full blown. Outer petals reflex and quill sharply to points. Spiral arrangement of petals remains distinct.
(4) *Petalage.*—Number of petals under normal conditions — about 23–27.
(5) *Color.*—After sepals fall and petals unfurl, flowers are well formed exhibition style and of red coloring in the range of 53D to 53B. Coloring of petal top surface tends closer to 53D. Coloring of petal undersurface is lighter toned and with some pale streaking, near 54D. Lower petal segment approaching point of petal attachment is yellow, near 10D which color also washes into the red color of petal undersurface.

C. Petals:
(1) *Texture.*—Thick.
(2) *Appearance.*—Inside velvety and outside satiny.
(3) *Form.*—Broad, fan shaped.
(4) *Arrangement.*—Regularly arranged.
(5) *Petaloids in center.*—Few.
(6) *Persistence.*—Drop off cleanly.
(7) *Fragrance.*—None.
(8) *Lasting quality.*—Long lasting quality on plant and as cut flower.

REPRODUCTIVE ORGANS

A. Stamens, filaments and anthers:
*Arrangement and color.*—Regularly arranged around styles. Color — filaments near 13B.

B. Pollen:
*Color.*—Near 23B.

C. Styles: Medium, even, bunches.

D. Stigmas:
*Color.*—Near 1C.

E. Hips: None observed.

PLANT

A. Form: Upright-bushy.

B. Growth: Very vigorous.
*Height attained.*—About 14–18 inches.

C. Foliage: Compound 5 to 7 leaflets.
(1) *Size.*—Medium.
(2) *Quantity.*—Abundant.

(3) *Color.*—New foliage: Upper side — near 183A. Under side — near 184A. Old foliage: Upper side — near 139A. Under side — near to 138B.

(4) *Shape.*—Oval, pointed.

(5) *Texture.*—Upper side is semiglossy; under side is matte.

(6) *Edge.*—Serrate.

(7) *Serration.*—Ordinary.

(8) *Leaf stem.*—Color — near to 183B. Under side — near 146C.

(9) *Stipules.*—Medium, not bearded.

(10) *Resistance to disease.*—Blackspot — Average. Mildew — Average. Rust — Average.

D. Wood:

(1) *New wood.*—Color — near 184A. Bark — smooth.

(2) *Old wood.*—Color — near 146C. Bark — smooth.

E. Thorns:

(1) *Thorns.*—Quantity (main stalk) — ordinary. On laterals from stalk — ordinary. Form — long, thin, curved slightly downward. Length — medium. Color — near 181A. Position — irregular.

(2) *Prickles.*—Average.

F. Winter hardiness: Needs protection in severe climate.

I claim:

1. A new and distinct variety of rose plant of the miniature rose class, substantially as shown and described, characterized particularly by red flowers of exhibition form which are long lasting on the plant and as cut flowers.

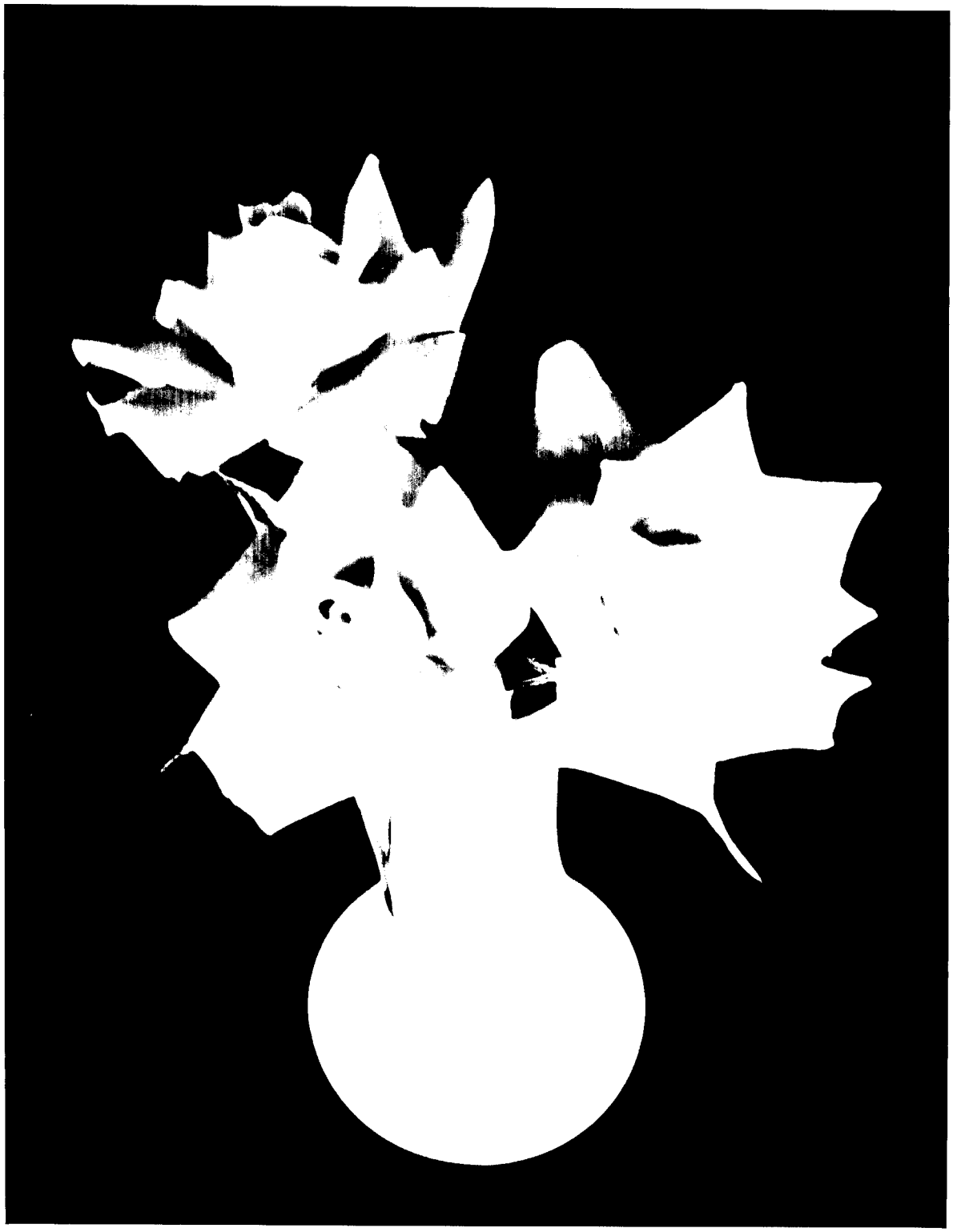

* * * * *